(12) United States Patent
Bui et al.

(10) Patent No.: US 6,977,084 B2
(45) Date of Patent: *Dec. 20, 2005

(54) **PET FOOD CONTAINING *PERNA CANALICULUS* FOR MAINTENANCE OF JOINT HEALTH AND ALLEVIATION OF ARTHRITIC SYMPTOMS**

(76) Inventors: Linh M. Bui, 12244 Via Santa Marta, Sylmar, CA (US) 91342; Tiffany L. Bierer, 2582 Associated Rd. #9, Fullerton, CA (US) 98235; Jason Hodge, 2 Albert Street, Port Lonsdale (AU), 3225; Roger Bektash, Arandel Park RMB 3060, Barnawartha (AU), 3688; Graeme Blackwood, 1721 Arbolita Dr., La Habra, CA (US) 90631

( * ) Notice: Subject to any disclaimer, the term of this patent is extended or adjusted under 35 U.S.C. 154(b) by 263 days.

This patent is subject to a terminal disclaimer.

(21) Appl. No.: 10/357,607

(22) Filed: Feb. 4, 2003

(65) Prior Publication Data

US 2003/0124219 A1 Jul. 3, 2003

Related U.S. Application Data

(63) Continuation of application No. 09/273,933, filed on Mar. 22, 1999, now Pat. No. 6,596,303.

(51) Int. Cl.$^7$ ............................. A23G 3/30; A23K 1/17; A23K 1/18; A23K 1/165; A01N 63/00

(52) U.S. Cl. ..................... 424/442; 424/93.4; 424/93.7; 424/520; 424/538; 424/547; 426/2; 426/6; 426/805

(58) Field of Search .............................. 424/93.4, 93.7, 424/520, 538, 547, 442, 439; 426/2, 6, 805

(56) References Cited

U.S. PATENT DOCUMENTS

| | | | |
|---|---|---|---|
| 4,455,298 A | 6/1984 | McFarlane et al. | |
| 4,801,453 A | 1/1989 | Kosuge et al. | |
| 5,364,845 A | 11/1994 | Henderson | |
| 5,587,363 A | 12/1996 | Henderson | |
| 5,843,919 A | 12/1998 | Burger | |
| 6,083,536 A | 7/2000 | Macrides et al. | |

FOREIGN PATENT DOCUMENTS

| | | |
|---|---|---|
| EP | 0010061 | 9/1979 |
| EP | 0982034 A1 | 3/2000 |
| JP | 03080079 | 8/1989 |
| NZ | 270754 | 8/1997 |
| RU | 2017439 C1 | 8/1994 |
| RU | 2097982 C1 | 12/1997 |
| WO | PC-94/22453 | 10/1994 |
| WO | PC-96/05164 | 2/1996 |
| WO | PC-97/09992 | 3/1997 |
| WO | PC-97/21434 | 6/1997 |

OTHER PUBLICATIONS

Healtheries of New Zealand Limited First Amended Notice of Opposition Jul. 8, 2004 to Grant of Patent Search (Section 21), In the matter of New Zealand Patent Application No. 514389 in the name of Kal Kan Foods, Inc. and in the matter of an opposition thereto by Healtheries of New Zealand Ltd., New Zealand Patent Office.

Waitaki Biosciences International Limited First Amended Notice of Opposition Jul. 8, 2004 to Grant of Patent Search (Section 21), In the matter of New Zealand Patent Application No. 514389 in the name of Kal Kan Foods, Inc. and in the matter of an opposition therto by Healtheries of New Zealand Ltd., New Zealand Patent Office.

Healtheries of New Zealand Limited First Amended Statement of Case (Jul. 8, 2004), In the matter of New Zealand Patent Application No. 514389 in the name of Kal Kan Foods, Inc. and in the matter of an opposition thereto by Healtheries of New Zealand Ltd., New Zealand Patent Office.

Affirmation of John Eric Croft, In the matter of New Zealand Patent Application No. 514389 in the name of Kal Kan Foods, Inc. and in the matter of an opposition thereto by Healtheries of New Zealand Ltd., New Zealand Patent Office.

Waitaki Biosciences International Limited First Amended Statement of Case (Jul. 8, 2004), In the matter of New Zealand Patent Application No. 514389 in the name of Kal Kan Foods, Inc. and in the matter of an opposition thereto by Healtheries of New Zealand Ltd., New Zealand Patent Office.

Letter from AJ Park Forwarding First Amended Statement of Case and First Amended Notice of Opposition from Healtheries of New Zealand Limited and Waitaki Biosciences International Limited dated Jul. 8, 2004.

Waitaki Biosciences International Limited, "Statement of Case," In the matter of an application for Letters Patent No. 514389 in the name of Kal Kan Foods, Inc. and in the matter of a Section 21 pregrant opposition theretoby Waitaki Biosciences Intenational Ltd, New Zealand Patent Office.

Healtheries of New Zealand Limited, "Statement of Case," In the matter of application for Letters of Patent No. 514389 in the name of Kal Kan Foods, Inc. and in the matter of a Section 21 pregrant opposition thereto by Healtheries of New Zealand Ltd., New Zealand Patent Office.

(Continued)

*Primary Examiner*—David M. Naff
*Assistant Examiner*—Deborah K. Ware
(74) *Attorney, Agent, or Firm*—Fulbright & Jaworski L.L.P.

(57) ABSTRACT

A pet food product and process for producing the pet food product for use in maintenance of healthy joints and alleviation of arthritic symptoms in companion animals, the pet food comprising an effective amount of an active extract of *Perna canaliculus*. The extract can be either a powder or lipid extract. Preferably in an amount that provides for a dosage range of generally 0.18 to 114 mg of a powder extract/kg of body weight/day in a companion animal or an amount of generally 1.5 to 1000 mg of a powder extract of *Perna canaliculus* per 400 kcal of pet food product.

11 Claims, 1 Drawing Sheet

OTHER PUBLICATIONS

Kal Kan Foods, Inc. "Counterstatement," In the matter of New Zealand Patent Application No. 514389 in the name of Kal Kan Foods, Inc. and in the matter of an opposition thereto by Healtheries of New Zealand Ltd., New Zealand Patent Office.

Kal Kan Foods, Inc. "Counterstatement," In the matter of New Zealand Patent Application No. 514389 in the name of Kal Kan Foods, Inc. and in the matter of an opposition thereto by Waitaki Biosciences International Ltd, New Zealand Patent Office.

McFarlane Laboratories NZ Ltd. Product Label—McFarlane SF6 The Seatone Formula for Horses.

Chassot Product Information for "Bihorsan" Pellets for horses.

Chassot product information for "Cartiflex".

Ford, G.R. "Experience with SF6 at Footbridge" Jul. 14, 1995.

Animal Health Services Centre—Massey University, "Final report on the Efficacy of Green–Lipped Mussel Extract in the Management of Degenerative Joint Disease in Dogs," Study No. AHSC–75353, Sep. 1999.

Chassot product information for CHASSOTON Granules 4%.

Gibson et al, "Perna canaliculus in the treatment of arthritis," Practitioner 224, No. 1347, pp. 995–960 (Sep. 1980).

Orima et al, "Clinical Effects of the extract of the New Zealand Green– Lipped Mussel on Dogs and Cats with Joint Diseases," Small Animal Veterinarys Clinic vol. 17, No. 1, Jan. 1998.

Croft, John E. The New Zealand Green–Lipped Mussel (3 ed., Thorsons, London, 1995) pp. 38–50, 57–85, 122–122.

McFarlane Laboratories SF4 & SF6—Scientific Information—released by McFarlane Laboratories.

Welsner, Christof of Masterhorse Service, letter to Waitaki Biosciences International, Ltd, Jun. 4, 1996.

Mussels bring Arthritis Relief, Veterinary Practice Jan. 7, 1985.

McFarlane Product Information for Green Liped Mussel Extract.

Product Information for McFarlane SF6 The Seatone Formula for Horses.

McFarlane Product Label for SF4 for Cats—Green Lipped Mussel Extract.

McFarlane Product Label for SP4 for Dogs—Green Lipped Mussel Extract.

Product Information in respect of CANOSAN concentrate and pellets for dogs.

Miller et al, "Evaluation of the Effect of Seatone Administration on Cell–Mediated Immune Mechanisms Determined Using in Vitro and in Vivo Analysis of T Lymphocyte Function,".

Chassot Product Information for CANOSAN Concentrate Granules.

Chassot Product Information for CANOSAN Pellets.

European Search Report.

Miller, Thomas, et al.; In vivo evidence for prostaglandin inhibitory activity in New Zealand green–lipped mussel extract; New Zealand Med. J.; pp 355–357, Jun. 13, 1984.

Kosuge, Takuo, et al.; Isolation of an Anti–histaminic Substance from Green–Lipped Mussel (perna canaliculus); Chem. Pharm. Bull., vol. 34 (11): 4825–4828, 1986.

McFarlane, S. J.; Green Mussel and Rheumatoid arthritis; New Zealand Med. J., p. 569, Jun. 25, 1975.

Miller, T. E.; Anti–Inflammatory effects of mussel extracts; New Zealand Med. J., pp. 23–24, Jan. 14, 1981.

COSEQUIN* and COSEQUIN* DS Advertisement.

Bennett, David, et al.; Textbook of Veterinary Internal Medicine: Diseases of the Dog and Cat: Chapter 149 Joint Diseases of Dogs and Cats; pp. 2032–2075.

Korthauer, Walter, et al.; Behandlung deformierender Arthropathien beim Diensthund mit einem neuen Glykosaminoglykanpraparat; Kilentierpraxis 37, pp. 467–478, Jan. 1992.

Volker, Dianne, et al.; Dietary N–3 Fatty Acid Supplementation in Rheumatoid Arthritis—Mechanisms, Clinical Outcomes, Controversies, and Future Directions; J. Clin. Biochem. Nutr. 20, pp. 83–97, 1996.

Kremer, Joel M., et al.; Dietary Fish Oil and Olive Oil Supplementation in Patients with Rheumatoid Arthritis—Clinical and Immunological Effects; Arthritis and Rheumatism 33 (6), pp. 810–820, Jun. 1990.

Winter, Charles A., et al.; Carrageenin–Induced Edema in Hind Paw of the Rat as an Assay for Anti–inflammatory Drugs; Merck Institute for Therapeutic Research, pp. 544–547, West Point, PA.

Cullen, J. C., et al.; The Effectof Dried Mussel Extract on an Induced Polyarthritis in Rats; New Zealand Med. J., pp. 260–261, Mar. 12, 1975.

Miller, Thomas E., et al.; The anti–inflammatory activity of Perna canaliculus (NZ green lipped mussel); New Zealand Med. J. 97; 667; pp. 187–193 (Sep. 10, 1980).

Rainsford, K. D., et al.; Gastroprotective and Anti–inflammatory Properties of Green Lipped Mussel (perna canaliculus) Preparation; Arzneim.–Forsch./Drug Res. 30 (II) Nr. 12, pp. 2128–2132, 1980.

Whitehouse, M. W., et al.; Anti–Inflammatory Activity of a Lipid Fraction (Lyprinol) from the NZ Green–Lipped Mussel; Inflammopharmacology 5: 237–246, 1997.

PET FOOD CONTAINING *PERNA CANALICULUS* FOR MAINTENANCE OF JOINT HEALTH AND ALLEVIATION OF ARTHRITIC SYMPTOMS

This application is a continuation of U.S. application Ser. No. 09/273,933 filed on Mar. 22, 1999 now U.S. Pat. No. 6,596,303.

FIELD OF THE INVENTION

The present invention relates to pet food for companion animals, and more particularly to pet food that includes an active quantity of an extract of *Perna canaliculus* in an amount that will provide a daily pet diet for the maintenance of joint health and for the alleviation of arthritic symptoms in companion animals such as dogs, cats and horses.

BACKGROUND OF THE INVENTION

The connective tissues of humans and non-human animals are constantly subject to stresses and strains from mechanical forces that can result in afflictions, such as arthritis (both rheumatoid and osteoarthritis), joint inflammation and stiffness. This is true for both humans and non-human animals, and particularly as they age. The underlying causes of rheumatoid arthritis and/or osteoarthritis are different such that rheumatoid arthritis is characterized as an autoimmune disease affecting both the joints and systemic immune functions, whereas osteoarthritis results from deterioration of the articular cartilage which may result in local inflammation of the joints. While a greater portion of humans with arthritis have rheumatoid arthritis, most of the arthritis occurring in companion animals is osteoarthritis.

In osteoarthritis or degenerative joint disease, increased stress in the joints results in loss of the integrity of the cartilage matrix and the resulting damage causes the accelerated destruction of cartilage components and synovial fluid. The connective tissues are naturally equipped to repair themselves by manufacturing and remodeling prodigious amounts of collagen (a chief component of connective tissue) and proteoglycans—the other major component of connective tissues. With aging, there is a decreased ability to restore and synthesize normal collagen structures. This results in pain, deformity and limitation of joint motion.

In dogs, osteoarthritis is a disorder of the synovial joints which is characterized by degeneration of the articular cartilage and by formation of new bone at the joint margins. Hardening of the underlying subchondral bone may also be a feature of osteoarthritis and in some cases, a variable degree of synovial inflammation may be present at some time during the progression of the disease.

The treatment of connective tissue afflictions in both humans and non-human animals can be quite problematic. A simple decrease in the stresses to which the connective tissue is subject is often not usually an option. Consequently, treatment is often directed at controlling the symptoms of the afflictions and not their causes, regardless of the stage of the degenerative process. Presently, steroids such as corticosteroids and other anti-inflammatory materials, such as high doses of aspirin are widely used for the treatment of these afflictions in humans. In veterinary medicine, hyaluronic acid and polysulfonated gylcosaminoglycan are used, particularly for equines to reduce connective tissue pain and swelling. While these materials often relieve the pain and swelling associated with maladies arising from connective tissue problems, almost all drugs eventually lose their effectiveness.

Natural products derived from plants and food have frequently been the source of effective drugs, and in recent years there has been an increased interest in the analysis of these natural products, especially where a clinical benefit is claimed. Compounds that have been identified in foods and may be of clinical benefit are the orally administered chondroprotective agents, glucosamine and chondrotin sulphate, which in the body, are normal constituents of articular cartilage. There are studies to suggest that these agents might be effective in humans in the treatment of osteoarthritis. However, there are few reports in the veterinary literature of the clinical efficacy of these oral chondroprotective agents in dogs and other animals.

In the category of natural food products, it has been found that certain marine organisms contain compounds that when fed to animals aid in the treatment of inflammation. One of these marine organisms is *Perna canaliculus* (New Zealand Green Lipped Mussel) in which its anti-inflammatory activity was first identified in a clinical study on leukemia.

Initial assessment of the anti-inflammatory activity of *Perna canaliculus* was first attempted using a polyarthritis model in rats. (Cullen et al. 1975.) These studies, however, failed to show the presence of any significant anti-inflammatory activity in the mussel preparation. In contrast, Miller and Ormrod (1980), using a carrageenan-induced paw edema assay (Winter et al. 1962), were able to show that mussel preparations, when administered intraperitoneally, gave a significant reduction to the swelling of a carrageenan-inducted rat paw edema. Subsequently, they fractionated a non-dialysable, water-soluble fraction from the mussel preparation that possessed the anti-inflammatory activity. The aqueous extract showed a dose-dependent anti-inflammatory activity when administered intraperitoneally which could not be detected upon oral administration of the mussel powder. It was suggested that the water-soluble fraction therefore contained an irritant component possessing apparent anti-inflammatory activity.

Rainsford and Whitehouse (1980) also reported that freeze-dried powder preparations of the whole mussel given orally to rats showed some modest anti-inflammatory activity in the carrageenan-induced paw edema assay, and that this material strikingly reduced the gastric ulcerogenicity of several non-steroidal anti-inflammatory drugs in rats and pigs. In another study, Korthauer and Delatorre (1992) found that the oral administration of a glycosaminoglycan extracted from *Perna canaliculus* to 26 dogs with arthritis at 10 mg/kg daily for eight weeks alleviated the signs of lameness or faulty posture in a high proportionate number of dogs in the study.

Macrides and Kalafatis, the named inventors of WO 96/05164 for an anti-inflammatory preparation, have established that lipid fractions from *Perna canaliculus* (in contrast to earlier work on aqueous fractions) are a rich source of compounds which in semipurified extracts, have shown a measure of anti-inflammatory activity when tested in appropriate model systems. In WO 96/05164, a purified active fraction isolated from a lipid extract of *Perna canaliculus* or *Mytilus edulis*, has an active component that has been shown to have anti-inflammatory properties. From this active component, a substantially pure form of 5,11,14,17-eicosatetraenoic acid (an omega 3 fatty acid) has been isolated and pharmaceutically acceptable esters, amides and salts thereof have been identified. This compound may be a major constituent of the active fraction isolated from the lipid extract of *Perna canaliculus*. The lipid extract when fed orally has been shown to reduce inflammation in rats. (Whitehouse et al. 1996.)

While the exact mechanism of *Perna canaliculus* on arthritic symptoms is unknown, it is thought to be partly due to the presence of a unique eicosatetraenoiec acid (ETA) as well as other unique fatty acids that appear to alter the production of inflammatory agents in the body via the lipoxygenase pathway. As previously discussed, the lipid extract of *Perna canaliculus* contains a high percentage of these fatty acids and the powder form contains small amounts of the same fatty acids as well as other nutrients such as complex proteins, glycosaminoglycans, vitamins, minerals and amino acids, that may act in synergism to regenerate damaged articular cartilage and synovial fluid. In understanding the ideology of the two main types of arthritis, the lipid extract may be more affective in treating animals and/or individuals with rheumatoid arthritis since studies have shown that omega-3 fatty acids can reduce synovial and systematic inflammatory response. (Volker et al. 1996.) As for the powder form, it may be more beneficial in treating individuals with osteoarthritis since it also contains glycosaminoglycans and other nutrients that might potentially help to regenerate articulate cartilage in the joints. These compounds may also help to maintain joint health in animals not yet exhibiting arthritic symptoms.

Based on the apparent effectiveness of a *Perna canaliculus* extract as an anti-inflammatory agent, it would be beneficial to provide a pet food that includes a quantity of an active extract of *Perna canaliculus* in an amount that will provide a pet diet for the maintenance of joint health and the alleviation of arthritic symptoms in companion animals such as dogs, cats and horses.

BRIEF SUMMARY OF THE INVENTION

An object of the present invention is a pet food product that includes an active extract of *Perna canaliculus* for the maintenance of joint health in companion animals.

An additional object of the invention is a pet food product that includes an active extract of *Perna canaliculus* for the alleviation of arthritic symptoms in companion animals.

A further object of the invention is a process for producing a pet food product that includes an active extract of *Perna canaliculus* for the maintenance of joint health and the alleviation of arthritic symptoms in companion animals.

An additional object of the invention is a process of feeding companion animals a diet comprising a pet food product containing an effective amount of an active extract of *Perna canaliculus* for the maintenance of joint health and alleviation of arthritic symptoms in companion animals.

Thus, in accomplishing the forgoing objects there is provided in accordance with one aspect of the present invention, a pet food product for companion animals that comprises an effective amount of an active extract of *Perna canaliculus* for the maintenance of joint health and alleviation of arthritic symptoms in companion animals. In specific embodiments the extract can be either a powder or lipid extract.

In additional embodiments, the invention includes a process for producing a pet food product for companion animals that includes the step of adding an effective amount of an active extract of *Perna canaliculus* to the pet food product for the maintenance of joint health and alleviation of arthritic symptoms in companion animals. The extract of *Perna canaliculus* maintains its activity throughout the process of production.

Another specific embodiment includes a process for maintaining joint health and alleviating arthritic symptoms in companion animals by feeding the companion animal a diet comprising a pet food product containing an effective amount of an active extract of *Perna canaliculus* for the maintenance of joint health and alleviation of arthritic symptoms in companion animals.

A further specific embodiment includes a pet food product comprising an active powder extract of *Perna canaliculus* in an amount that provides for a dosage range of generally 0.18 to 114 mg of powder extract/kg of body weight/day in a companion animal.

Another specific embodiment includes a pet food product comprising generally 1.5 to 1000 mg of active powder extract of *Perna canaliculus* per 400 kcal of pet food product.

A further specific embodiment includes a pet food product including a lipid extract in an amount that provides for a dosage range of generally 1.0 to 13 mg of lipid extract/kg/day in a companion animal.

Another specific embodiment includes a pet food product including a lipid extract in an amount that provides for about 10.0 to 100 mg of active lipid extract of *Perna canaliculus* per 400 kcal of pet food product.

Other and further objects, features, and advantages will be apparent from the following description of the presently preferred embodiments of the invention, which are given for the purpose of disclosure.

DETAILED DESCRIPTION OF THE INVENTION

Figure 1:
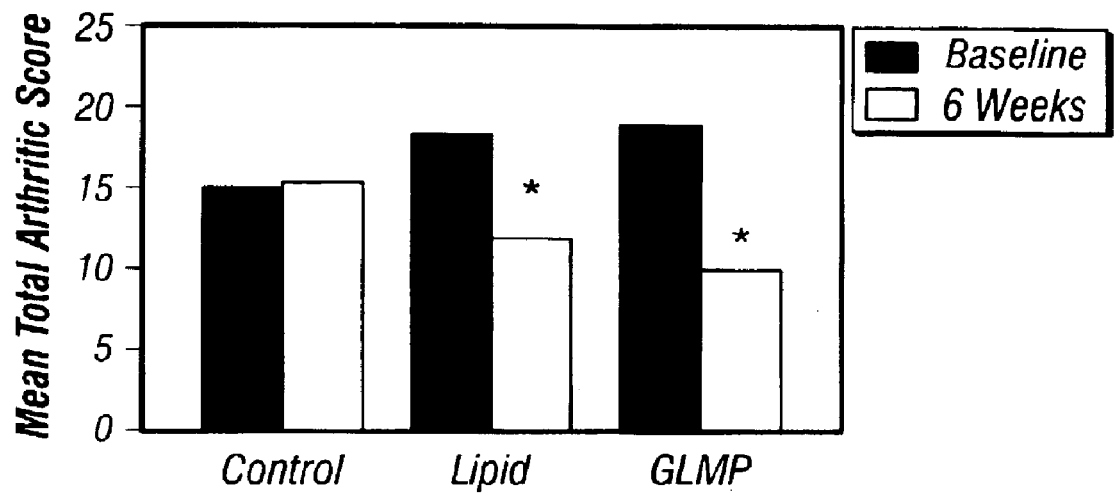
FIG. 1 shows the influence of Green Lipped mussel on arthritic symptoms at 0 and 6 weeks of treatment. *,+ Represents significant differences from baseline scores ($p > 0.05$).

The present invention is directed to pet food products such as wet and semi-moist pet food, dry kibble, treats and a pet drink that contain an effective amount of an active extract of *Perna canaliculus* for maintaining joint health and alleviating arthritic symptoms in companion animals such as dogs, cats and horses.

Although the underlying mechanism in alleviating arthritic symptoms by extracts of *Perna canaliculus* (Green Lipped Mussel) have not been well characterized, it has been shown that extracts of *Perna canaliculus* in both the powder and lipid form are efficacious in alleviating arthritic symptoms in dogs. Even though both the powder and lipid extracts have been found to be effective, the Green Lipped Mussel powder (GLMP) may be a more efficacious treatment for osteoarthritic animals because it helps address both a cause (regeneration of cartilage and synovial fluid) and effect (anti-inflammatory effects) of osteoarthritis.

An "extract" of *Perna canaliculus* is considered to be either a powdered form of the entire *Perna canaliculus* or a concentrated preparation of the lipid portion of the *Perna canaliculus*.

A compound or composition is said to be "acceptable" if its administration can be tolerated by a recipient mammal.

Such an agent is said to be administered in an "effective amount" if the amount administered is physiologically significant. An agent is physiologically significant if its presence results in technical change in the physiology of a recipient mammal. For example, in the alleviation of arthritic symptoms in companion animals, an agent which slows the progression of the disease and/or symptoms or completely treats the disease and/or symptoms, would be considered effective.

The dosages given as examples herein are the dosages determined by the studies. The dosages administered are an effective amount of active ingredient and will, of course, vary depending upon known factors such as the pharmacodynamic characteristics of the particular active ingredient and its mode and route of administration; the age, sex, health and weight of the companion animal; nature and extent of symptoms; kind of concurrent treatment, frequency of treatment and the effect desired.

A daily dosage (effective amount) in a range of about 0.18 to 114 mg of active GLMP/kg of body weight/day is efficacious in alleviating arthritic symptoms in companion animals and likewise would also maintain joint health. More preferably, a dosage range of 1.8 to 85 mg of GLMP/kg of body weight/day, and most preferably, a dosage range of 9 to 58 mg of GLMP/kg of body weight/day would be efficacious in maintaining joint health and alleviating arthritic symptoms in companion animals. This dosage equates to a 22 kg dog receiving 0.45 g/day or 0.02 g/kg of body weight/day of GLMP. In a 454.5 kg horse, the dosage would be 10 g/day or 0.02 g/kg of body weight/day of GLMP. The dosage level for a cat would be the amount required to reach a level of 0.02 g/kg of body weight/day of GLMP.

The amount of active GLMP that is necessary per 400 kcal of a pet food product to be efficacious in maintaining joint health and alleviating arthritic symptoms in companion animals, and most particularly dogs, is generally 1.5 mg to 1000 mg of GLMP/400 kcal of pet food. More preferably an amount of 15 mg to 750 mg of GLMP/400 kcal and most preferably, an amount of 75 mg to 520 mg of GLMP/400 kcal of a pet food product to be efficacious in the maintenance of joint health and alleviating arthritic symptoms in companion animals.

A daily dosage (effective amount) of the lipid extract of about 1.0 to 13 mg/kg of body weight/day and a most preferred dosage of 4.6 to 5.1 mg/kg of body weight/day is efficacious in alleviating arthritic symptoms in companion animals and likewise would also maintain joint health. A dosage based on mg/400 kcal is about 10.0 to 100 mg of the lipid extract/400 kcal of pet food and more preferably, 33 to 40 mg of the lipid extract/400 kcal of a pet food product to be efficacious in the maintenance of joint health and alleviating arthritic symptoms in companion animals.

New and novel pet food products have been developed that contain an active extract of *Perna canaliculus* or its equivalent (i.e. an extract of *Mytilus edulis*), in an amount that is efficacious in maintaining joint health and alleviating arthritic symptoms in companion animals. As is known to one skilled in the art, there are a variety of commonly known pet food products. In the area of cat and dog food, there is wet pet food, semi-moist pet food, dry pet food and pet treats. Drinks for pets are also available such as milk drinks for cats. Wet pet food generally has a moisture content above 65%. Semi-moist pet food typically has a moisture content between 20–65% and can include humectants such as propylene glycol, potassium sorbate, and other ingredients to prevent microbial growth (bacteria and mold). Dry pet food (kibble) generally has a moisture content below 20% and its processing typically includes extruding, drying and/or baking in heat. Pet treats can typically be semi-moist chewable treats; dry treats in any number of forms; chewable bones; baked, extruded or stamped treats; confection treats; or other kinds of treats as is known to one skilled in the art. Horse food is typically dry and contains a mixture of cereals and supplements.

A semi-moist pet food product generally includes ingredients such as cereal grains, meats, fats, vitamins, minerals and functional ingredients that are blended together, cooked and packaged. However, any semi-moist pet food formulation known to one skilled in the art can be used. For example, a pet food of the subject invention can be formed by adding to a basic semi-moist pet food formulation, about 10% by weight of GLMP. In this example of a semi-moist pet food, 4.5 grams of food contains approximately 2910 kcal/kg, which will deliver a GLMP dosage range of 9 to 58 mg of GLMP/kg/day.

While a composition and process for producing a semi-moist pet food product has been generally described above, it should be appreciated that any semi-moist pet food composition and process known to one skilled in the art can be used to produce a semi-moist pet food product containing GLMP or the lipid portion.

In an example of a dry pet food, the ingredients generally include cereal grains, meats, poultry, fats, vitamins, minerals and other functional ingredients. The ingredients are mixed and put through an extruder/cooker. Thereafter, the product is cut or shaped and dried. After drying, flavors, fats and other functional ingredients can be coated or sprayed onto the dried product. The spray used is of a kind that is known to one skilled in the art of producing dry pet food. To produce an example of a dry pet food of the subject invention, GLMP is added to the product in the spraying process after it has been dried. This is achieved by incorporating GLMP into any known spray in an amount that would provide a final concentration of GLMP in a range of generally between 0.06% w/w and 4.2% w/w. A spray mixture having this amount of GLMP provides an inclusion level of generally 10% w/w of the GLMP. The intact dry food is then spray coated with the GLMP spray mixture in which the final product has an inclusion level of GLMP that is generally about 1% w/w or below. This example of a dry pet food will deliver about 3300 kcal/kg, which will give a GLMP dosage range of generally between 75 mg to 520 mg/400 kcal.

While a composition and process for producing a dry pet food product has been generally described above, it should be appreciated that any dry pet food composition and process known to one skilled in the art can be used to produce a dry pet food product suitable for coating with the GLMP or lipid portion.

A wet pet food and pet treats are produced as is known to one skilled in the art depending upon the kind of wet pet food product and treat desired. The procedure for adding the GLMP or lipid portion to any pet food product will depend upon the type of processing required to manufacture the wet pet food or treat. For example, in semi-moist treats, in which the processing temperature usually does not exceed 50–70 degrees C., the active GLMP or lipid portion can be added to the treat during processing. However, if the processing temperature of the treat generally exceeds 70 degrees C., then the active GLMP or lipid portion can be coated on the finished product.

The anti-arthritic activity of the *Perna canaliculus* extract has been shown to be sensitive to moisture, heat and light. Experimentation has demonstrated that extrusion cooking of the *Perna canaliculus* extract above 100 degrees C. destroys activity and that activity is only maintained with processing temperatures below 70 degrees C. In the processing of the semi-moist pet food, the temperature of processing has been restricted to temperatures below that of extrusion cooking. The GLMP added to the semi-moist product can be stabilized by the addition of anti-oxidant system composed of an organic acid and tocopherols such as tartaric acid and vitamin E if desired. In the dry food product, the GLMP or lipid portion is added to the surface of the product at low temperatures in conjunction with surface spray ingredients. The anti-arthritic activity of the *Perna canaliculus* extract is maintained throughout the manufacturing process in the semi-moist and dry pet food products and pet treats by using this low temperature, stabilization criteria. However, any method used to protect the *Perna canaliculus* extract from degradation during processing, such as encapsulation or new processing technology, can be used to produce the inventive pet food.

Thus, as described, the present invention is a pet food product for companion animals that includes a quantity of the active extract of *Perna canaliculus* in an effective amount that will provide a pet diet for the maintenance of healthy joints and alleviation of arthritic symptoms in companion animals. The extract can be in either powder or lipid form. The present invention also includes a process for producing the pet food product containing an amount of active *Perna canaliculus* extract and a process of feeding the companion animals the inventive pet food.

EXAMPLE 1

Influence of Green Lipped Mussel on Arthritic Symptoms

The effect of the *Perna canaliculus* extract in both powder and lipid form in alleviating osteoarthritic symptoms in dogs, was determined wherein forty-seven mixed breed and sex adult dogs, ranging in age from 8–12 years, were fed a base diet consisting of a mix of canned and dry food. The dogs were divided into three groups. A control group of 15 dogs was given a colored water placebo; another 15 dogs were given an oil supplement containing generally 80% mussel lipid extract, 20% olive oil and vitamin E; and the other 17 dogs were given GLMP. A lipid extract without the olive oil and vitamin E would provide the same effect. The dosage for the oil supplement group was 216 mg/day for dogs weighing >75 lbs; 192 mg/day for dogs weighing between 55 to 75 lbs; and 144 mg/day for dogs weighing <55 lbs. In the GLMP group, the dosage was 1000 mg/day for dogs weighing >75 lbs; 750 mg/day for dogs weighing between 55 to 75 lbs; and 450 mg/day for dogs weighing <55 lbs. The control group was dosed at 1 ml for dogs weighing <55 lbs and 2 ml for dogs weighing >55 lbs. The GLMP and lipid compounds were provided by McFarlane Laboratories Pty. Ltd., 410 Canterbury Rd., Surrey Hills, Victoria, 3127 Australia.

All dogs were assessed for arthritic symptoms visually and physically by a veterinarian at baseline and again at six weeks. Factors assessed at each time point included range of motion, mobility, pain swelling and crepitus. These factors were used to calculate total arthritic scores for the dogs. At the end of the six weeks, as shown in Table 1 and FIG. 1, the data showed that both the lipid and GLMP extract were efficacious in alleviating arthritic symptoms, however, more dogs in the GLMP group improved or had greater reduction in arthritic symptoms as compared to the lipid dosed group of dogs.

TABLE 1

| % Reduction in total arthritic scores | Control (n = = 15) | Lipid (n = 15) | GLMP (n = 17) |
|---|---|---|---|
| % of dogs with ≧30% reduction in total arthritic scores | 6.6% (1/15 dogs) | 46.7% (7/15 dogs) | 82.4% (14/17 dogs) |
| % of dogs with ≧50% reduction in total arthritic scores | 0.0% (0/15 dogs) | 20.0% (3/15 dogs) | 35.5% (6/17 dogs) |
| % of dogs with ≧70% reduction in total arthritic scores | 0.0% (0/15 dogs) | 13% (2/15 dogs) | 17.6% (3/17 dogs) |

EXAMPLE 2

The Influence of Different Dosages of GLMP on Total Arthritic Scores

A second study was performed to evaluate whether different dose levels of GLMP would alleviate arthritic symptoms in dogs at an earlier time point or at a lower dose level. In this study, forty-seven mixed breed and sex adult dogs, ranging in age from 8–12 years, were fed the same basic diet. The dogs were divided into four groups. A control group of 12 dogs was given a wheat flour placebo. A second group of 12 dogs was given a dosage of GLMP in an amount of 1000 mg/day for dogs weighing >75 lbs; 750 mg/day for dogs weighing between 55 to 75 lbs; and 450 mg/day for dogs weighing <55 lbs which was 100% of the dosage given in the initial study. A third group of 11 dogs was given a dosage of GLMP in an amount of 500 mg/day for dogs weighing >75 lbs; 375 mg/day for dogs weighing between 55 to 75 lbs; and 225 mg/day for dogs weighing <55 lbs, which was 50% of the dosage given in the initial study. A fourth group of 12 dogs was given a dosage of GLMP in the amount of 2000 mg/day for dogs weighing >75 lbs; 1500 mg/day for dogs weighing between 55 to 75 lbs; and 900 mg/day for dogs weighing <55 lbs, which was 200% of the dosage given in the initial study.

Figure 2:
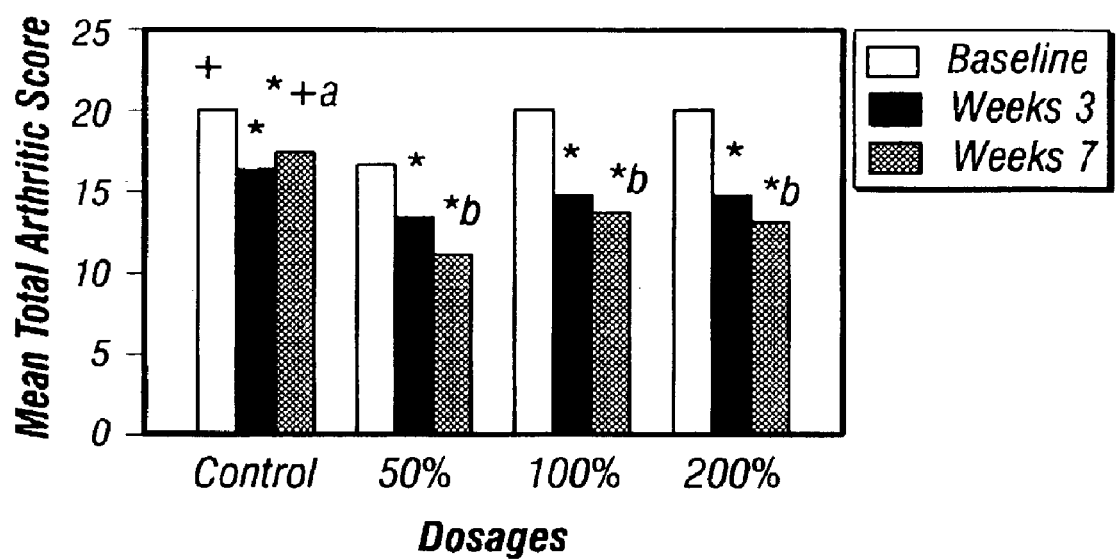
FIG. 2 shows the influence of different doses of Green Lipped Mussel powder (GLMP) on total arthritic scores at 3 weeks and 7 weeks. *,+ Represent differences only within each group between the timepoints at a level of $p < 0.05$. Significant differences were observed between the Baseline, 3 week and 7 week timepoints in the 50, 100 and 200% dosages. $^{a,b}$ Represent after 7 weeks of treatment; differences were observed between the control and the treatment group.

All dogs were assessed for arthritic symptoms visually and physically by a veterinarian at baseline and again at three and seven weeks using the criteria established in the initial study. As illustrated in Table 2 and FIG. 2, this study revealed that a statistically significant reduction in total arthritic score was found after seven weeks of treatment in the 50%, 100% and 200% dosage groups as compared to their respective baseline time points and to the seven week control group score. Additionally, all the test groups showed statistically significant reductions in total arthritic scores between their respective third week and baseline time points. In the control group, three week mean scores were significantly lower than baseline scores, but those differences were not seen at 7 weeks.

TABLE 2

| % Reduction in total arthritic scores | Control (0%) (n = 12) | GLMP (50%) (n = 11) | GLMP (100%) (n = 12) | GLMP (200%) (n = 12) |
|---|---|---|---|---|
| % of dogs with ≧30% reduction in total arthritic scores | 8.3% (1/12 dogs) | 64% (7/11 dogs) | 50% (6/12 dogs) | 50% (6/12 dogs) |
| % of dogs with ≧40% reduction in total arthritic scores | 0.0% (0/12 dogs) | 45% (4/11 dogs) | 33% (4/12 dogs) | 33% (4/12 dogs) |
| % of dogs with ≧50% reduction in total arthritic scores | 0.0% (0/12 dogs) | 27% (3/11 dogs) | 8.3% (1/12 dogs) | 25% (3/12 dogs) |
| % of dogs with ≧60% reduction in total arthritic scores | 0.0% (0/12 dogs) | 18% (2/11 dogs) | 0.0% (0/12 dogs) | 25% (3/12 dogs) |

One skilled in the art will readily appreciate that the present invention is well adapted to carry out the objects and obtain the ends and advantages mentioned, as well as those inherent therein. The inventive pet food products, methods for producing the pet food products, and methods for feeding the pet food products to companion animals for the maintenance of joint health and alleviation of arthritic symptoms in companion animals described herein are presently representative of the preferred embodiments, are exemplary, and are not intended as limitations on the scope of the invention. Changes therein and other uses will occur to those skilled in the art which are encompassed within the spirit of the invention and are defined by the scope of the claims.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference. All of the following references have been cited in this application:
WO 96/05164, Anti-Inflammatory Preparation, published Feb. 22, 1996.
Cullen, J. C., Flint, M. H., and Leider, J. (1975) M. Z. Med. J. 81:260–261.
Miller, T. E. and Ormrod, D. J. (1980), M. Z. Med. J. 92:187–193.
Winter, C. A., Risley, A. E. and Nuss, G. W. (1962) Prc. Soc. Exp. Biol. Med. 111:544–547.
Rainsford, K. D. and Whitehouse, M. W. (1980), Arzneim.-forsch./Drug Res. 30(ii), 2128–2132.
Korthauer, W. and Delatorre, J., Kleintierpraxis V. 37, No. 7; (1992) 467–768.
Whitehouse, M. W., Macrides, T. A., Kalafatis, N., Betts, W. H., Hayes, D. R., and Broadbent, J, (1997) Inflammmopharmacology 5:237–246.
Volker, D., Garg, M. (1996) J. Clin. Biochem. Nutr. 20:83–97; and Kramer, J. M., Lawrence, D. A., Jubiz, W., DiGiacomo, R., Rynes, R., Bartholomew, L. E., and Sherman, M. (1990), Arthritis and Rheumatism 33:810–820.

What is claimed is:

1. A pet food product, the pet food product comprising powdered entire *Perna canaliculus* for the maintenance of joint health and alleviation of arthritic symptoms in a companion animal selected from the group consisting of dog, cat and horse, wherein said pet food product contains an amount of the powdered entire *Perna canaliculus* such that feeding of the pet food product to said animal administers the powdered entire *Perna canaliculus* in an amount from about 0.18 to about 114 mg/kg of animal body weight/day to said animal.

2. The pet food product of claim 1 wherein the amount of powder administered is from about 9 to about 58 mg/kg of animal body weight/day.

3. The pet food product of claim 1 wherein the pet food product is selected from a group consisting of a wet pet food, a semi-moist pet food, a dry pet food, a pet treat and a pet drink.

4. The pet food product of claim 1 wherein the pet food product contains about 1.5 to about 1000 mg of said powder per 400 kcal of the pet food product.

5. The pet food product of claim 4 wherein the pet food product contains about 15 to about 750 mg of said powder per 400 kcal of the pet food product.

6. The pet food of claim 4 wherein the pet food product the pet food product contains about 75 to about 520 mg of said powder per 400 kcal of the pet food product.

7. A pet food product, the pet food product comprising a concentrated preparation of lipid portion of *Perna canaliculus* for the maintenance of joint health and alleviation of arthritic symptoms in a companion animal selected from the group consisting of dog, cat and horse, wherein said pet food product contains an amount of the concentrated preparation of lipid portion of *Perna canaliculus* such that feeding of the pet food product to said animal administers the concentrated preparation of lipid of *Perna canaliculus* in an amount from about 1 to about 13 mg/kg of animal body weight/day to said animal.

8. The pet food product of claim 7 wherein the amount of lipid portion administered is from about 4.6 to about 5.1 mg/kg animal body weight/day.

9. The pet food product of claim 7 wherein the pet food product is selected from a group consisting of a wet pet food, a semi-moist pet food, a dry pet food, a pet treat and a pet drink.

10. The pet food product of claim 7 wherein the pet food product contains about 10 to about 100 mg of said lipid portion per 400 kcal of the pet food product.

11. The pet food of claim 10 wherein the pet food product contains about 33 to about 40 mg of said lipid portion per 400 kcal of the pet food product.

* * * * *